(12) United States Patent
Liu et al.

(10) Patent No.: US 9,259,030 B2
(45) Date of Patent: Feb. 16, 2016

(54) FABRICATION OF CORE/SHELL CAPSULES OF DIFFERENT GEOMETRIES AND TREATMENT THEREAFTER

(75) Inventors: Hongwei Liu, Appleton, WI (US); Georgios D. Karles, Richmond, VA (US); Shuzhong Zhuang, Richmond, VA (US); Jose Nepomuceno, Beaverdam, VA (US)

(73) Assignee: PHILIP MORRIS USA INC., Richmond, VA (US)

( * ) Notice: Subject to any disclaimer, the term of this patent is extended or adjusted under 35 U.S.C. 154(b) by 1258 days.

(21) Appl. No.: 13/071,737

(22) Filed: Mar. 25, 2011

(65) Prior Publication Data

US 2012/0024305 A1    Feb. 2, 2012

(51) Int. Cl.
*A24B 15/28* (2006.01)
*A23L 1/48* (2006.01)
*A61K 9/48* (2006.01)
*A23L 1/22* (2006.01)

(52) U.S. Cl.
CPC ............ *A24B 15/283* (2013.01); *A23L 1/22008* (2013.01); *A23L 1/22016* (2013.01); *A61K 9/48* (2013.01); *A24B 15/284* (2013.01)

(58) Field of Classification Search
CPC ............... A24B 15/283; A24B 15/284; A23L 1/22016; A23L 1/22008; A61K 9/48
USPC ..................................................... 264/173.12
See application file for complete search history.

(56) References Cited

U.S. PATENT DOCUMENTS

| | | | |
|---|---|---|---|
| 2,275,154 A | 3/1942 | Merrill et al. | |
| 3,389,194 A | 6/1968 | Somerville | |
| 4,389,419 A | 6/1983 | Lim et al. | |
| 4,755,377 A | 7/1988 | Steer | |
| 4,816,259 A | 3/1989 | Matthews et al. | |
| 4,880,646 A * | 11/1989 | Lew et al. | 426/93 |
| 4,888,140 A | 12/1989 | Schlameus et al. | |
| 5,227,298 A | 7/1993 | Weber et al. | |
| 5,478,508 A | 12/1995 | Suzuki et al. | |
| 5,531,735 A | 7/1996 | Thompson | |
| 5,635,609 A | 6/1997 | Levy et al. | |

(Continued)

FOREIGN PATENT DOCUMENTS

CN    2610671 Y    4/2004
CN    101385892 A    3/2009

(Continued)

OTHER PUBLICATIONS

International Preliminary Report on Patentability Issued Oct. 11, 2012 for PCT/IB2011/000824.

(Continued)

*Primary Examiner* — Anthony Calandra
(74) *Attorney, Agent, or Firm* — Buchanan, Ingersoll & Rooney PC

(57) ABSTRACT

Multi-shelled capsules are made by co-extruding a first liquid flavorant composition and a first shell-forming polymeric material to form droplets which are hardened to form an inner shell containing a first liquid flavorant composition, and then coated with a second shell-forming polymeric material which is hardened to form an outer shell. The result is a capsule where the inner surface of the outer shell is separate and/or separable from the outer surface of the inner shell to define a space, wherein a second liquid flavorant composition may be located.

23 Claims, 6 Drawing Sheets

(56) References Cited

U.S. PATENT DOCUMENTS

Figure 1A:
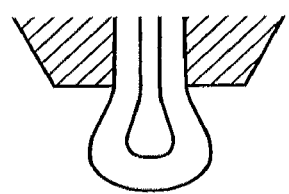

| | | |
|---|---|---|
| 6,020,200 A | 2/2000 | Enevold |
| 6,290,988 B1 | 9/2001 | Van Vilsteren et al. |
| 6,780,507 B2 | 8/2004 | Toreki et al. |
| 6,911,216 B1 | 6/2005 | Roth et al. |
| 6,991,804 B2 | 1/2006 | Helmus et al. |
| 8,235,056 B2 | 8/2012 | Zhuang et al. |
| 2003/0129248 A1 | 7/2003 | Pommersheim |
| 2004/0191366 A1 | 9/2004 | Mangos et al. |
| 2005/0067726 A1 | 3/2005 | Yan et al. |
| 2005/0172976 A1 | 8/2005 | Newman et al. |
| 2006/0144412 A1 | 7/2006 | Mishra et al. |
| 2006/0174901 A1* | 8/2006 | Karles et al. ......... 131/337 |
| 2007/0012327 A1 | 1/2007 | Karles et al. |
| 2007/0186941 A1 | 8/2007 | Holton, Jr. et al. |
| 2008/0017206 A1 | 1/2008 | Becker et al. |
| 2009/0004333 A1* | 1/2009 | Nakhasi et al. ......... 426/72 |
| 2010/0285118 A1* | 11/2010 | Dekker et al. ......... 424/456 |

FOREIGN PATENT DOCUMENTS

| | | |
|---|---|---|
| EP | 0 462 269 B1 | 12/1995 |
| EP | 1 221 839 B1 | 5/2004 |
| JP | 9-65853 A | 3/1997 |
| JP | 11-155480 A | 6/1999 |
| WO | WO 02/080672 A1 | 10/2002 |
| WO | WO 2005/041884 A2 | 5/2005 |
| WO | WO 2006/082529 A2 | 8/2006 |
| WO | WO 2007/010407 A2 | 1/2007 |
| WO | WO 2009/094859 A1 | 8/2009 |

OTHER PUBLICATIONS

Official Action dated Aug. 9, 2013 for Chinese Patent Appln. No. 201180016004.3.

Decision of Granting mailed Nov. 11, 2014 for corresponding Russian Patent Appln. No. 2012145452.

* cited by examiner

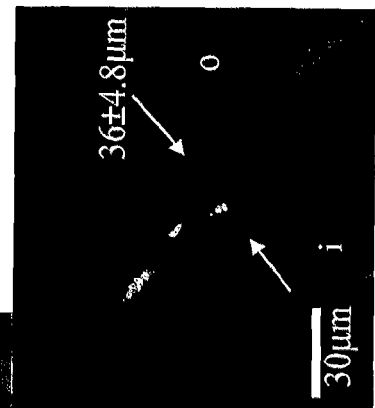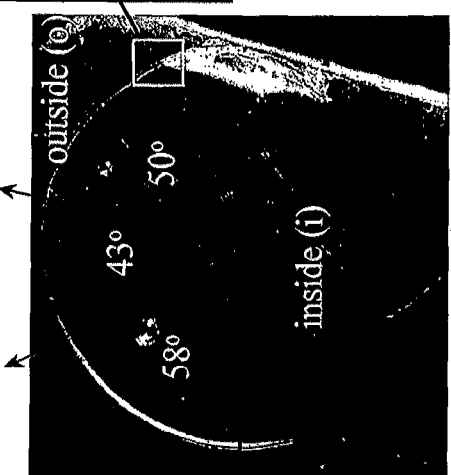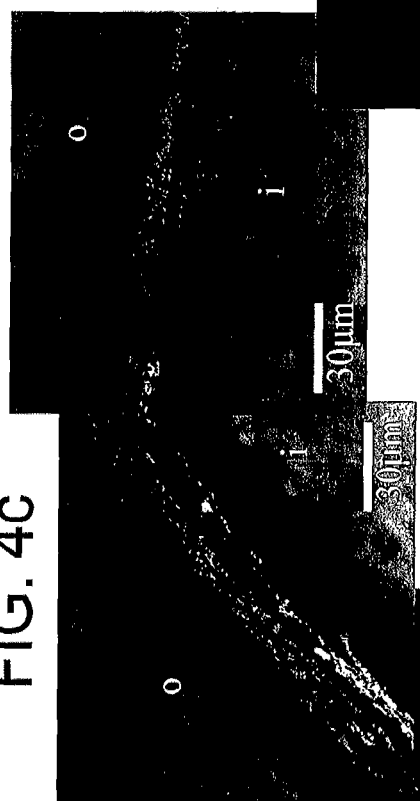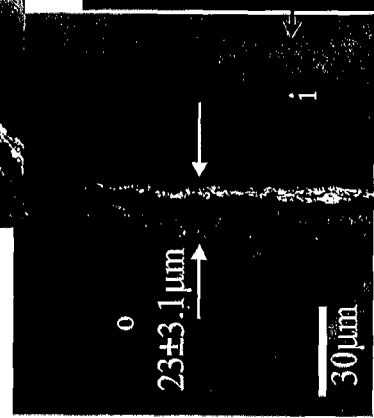

Gel with insoluble liquid

Liquid

Liquid

Liquid

FABRICATION OF CORE/SHELL CAPSULES OF DIFFERENT GEOMETRIES AND TREATMENT THEREAFTER

CROSS REFERENCE TO RELATED APPLICATION

This application claims priority under 35 U.S.C. §119(e) to U.S. Provisional Application No. 61/318,216, filed on Mar. 26, 2010, the entire content of which is incorporated herein by reference thereto.

BACKGROUND

Flavorants, e.g., compounds and compositions that provide pleasing tastes and aromas to other articles, are often incorporated into consumer products, such as smoking and smokeless articles, to increase the aesthetic enjoyment thereof. However, some flavorants are easily volatilized, escaping during storage and before the article is used.

It is desirable, therefore, to reduce or minimize migration and loss of flavorants in consumer products, and in particular in tobacco products, such as smoking articles and smokeless tobacco, so that a larger proportion of the applied flavorant is available to the consumer, even after the product has been stored for a period of time. In addition, it is desirable to provide flavorants to consumer products in such a way that multiple flavors can be applied, and their release characteristics controlled, in order to provide consumers with a consistently enjoyable experience.

SUMMARY

In one embodiment, a method for encapsulating a liquid flavorant composition in a multi-shelled capsule comprises: (a) co-extruding a first liquid flavorant composition and a first shell-forming polymeric material to form a core-shell droplet; (b) hardening the first shell-forming polymeric material of the droplet to form an inner shell around an inner core, the inner core comprising the first liquid flavorant composition; (c) coating the inner shell with a coating layer comprising a second shell-forming polymeric material to form an outer shell of the capsule; and (d) hardening the second shell-forming polymeric material by contacting the second shell-forming polymer with polyvalent metal ions present in or on the inner shell, to form an outer shell of the multi-shelled capsule.

Another embodiment is a multi-shelled capsule comprising: (a) an inner core comprising a first liquid flavorant composition, (b) an inner shell of a first polymeric material at least partially enclosing the inner core, (c) an outer shell of a second polymeric material at least partially enclosing the inner shell, and (d) a second liquid flavorant composition disposed in a space between the inner shell and the outer shell.

In addition to providing flavorant compositions that are storage-stable, that provide controlled release of flavorant, and which can provide multiple flavorants, the embodiments disclosed herein provide an improved co-extrusion method for encapsulating flavorants that yields improved mechanical stability of the capsules produced, by providing multiple encapsulating coatings. In addition, the embodiments disclosed herein provide improved consistency in capsule size, reduce or eliminate capsule aggregation, and allow for control of capsule geometry.

BRIEF DESCRIPTION OF THE DRAWING FIGURES

FIGS. 1(a), 1(b), 1(c), and 1(d) are schematic illustrations of co-extruded core-shell droplets at a nozzle according to embodiments disclosed herein.

Figure 2:
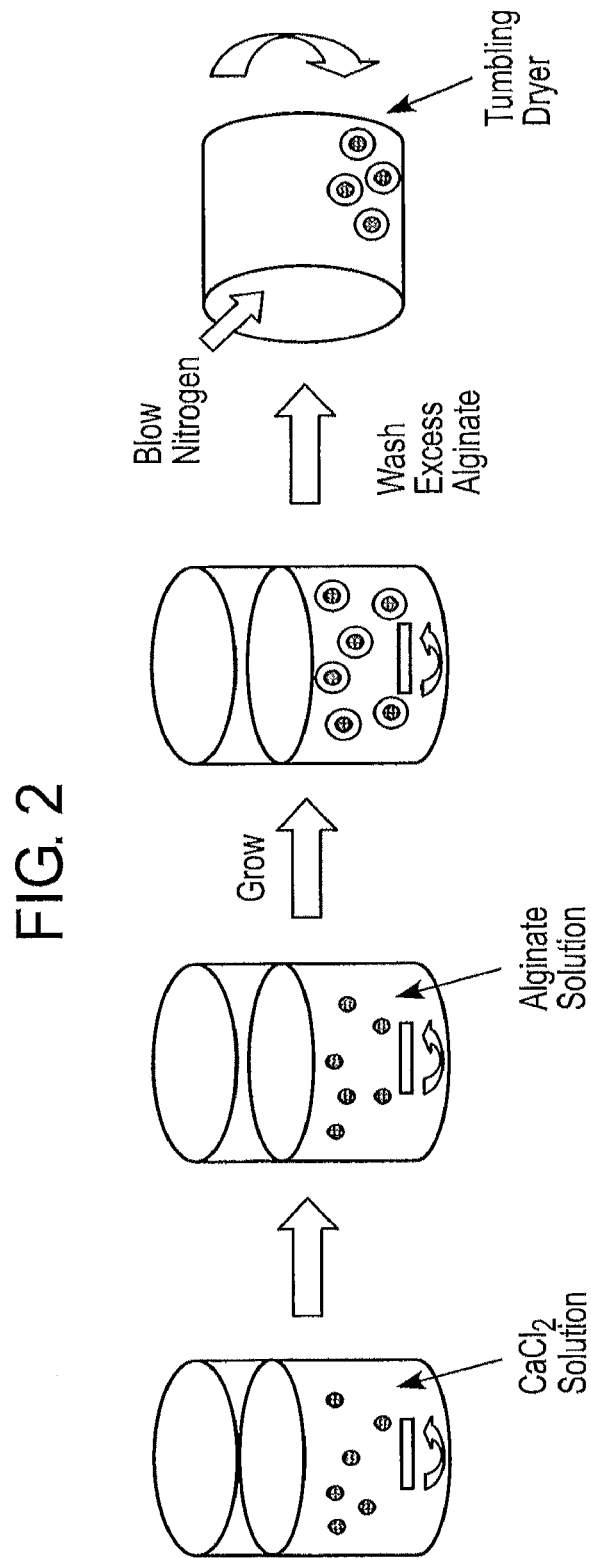

FIG. 2 is a schematic diagram showing a process for forming a multi-shelled capsule according to an embodiment disclosed herein.

Figure 3A:
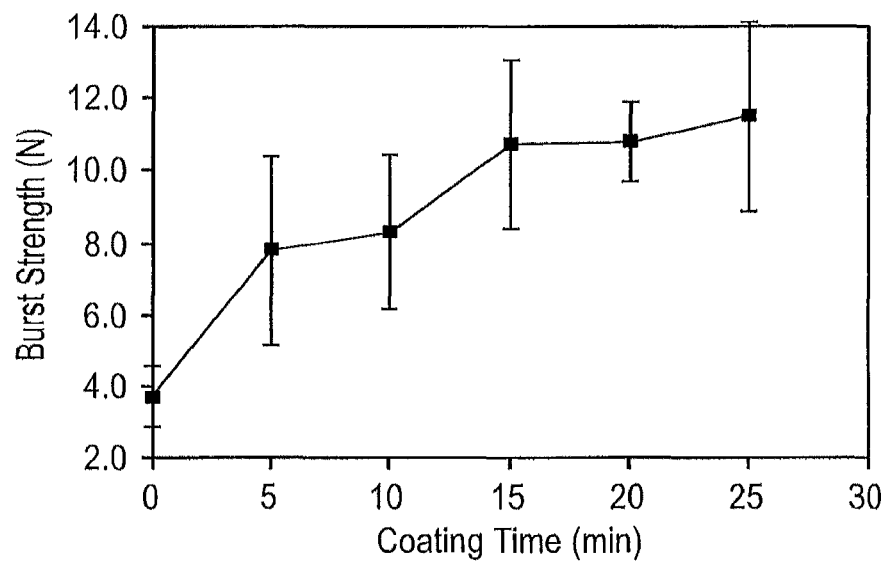
Figure 3B:
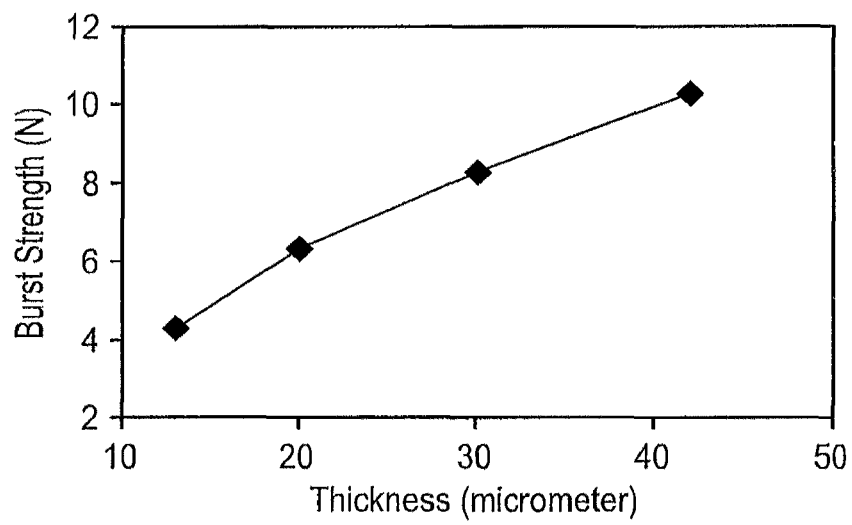

FIGS. 3(a) and 3(b) shows the increase in burst strength with coating time and capsule thickness according to embodiments disclosed herein.

FIGS. 4(a), 4(b), 4(c), 4(d), and 4(e) are photomicrographs showing a phase separation between the inner and outer shells of a multi-shelled capsule according to an embodiment disclosed herein.

Figure 5A:
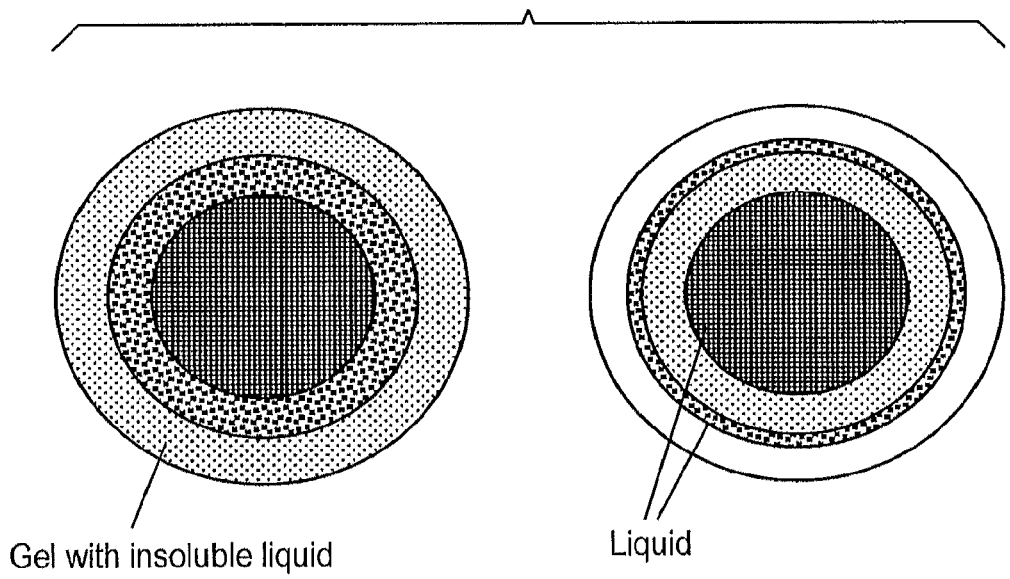
Figure 5B:
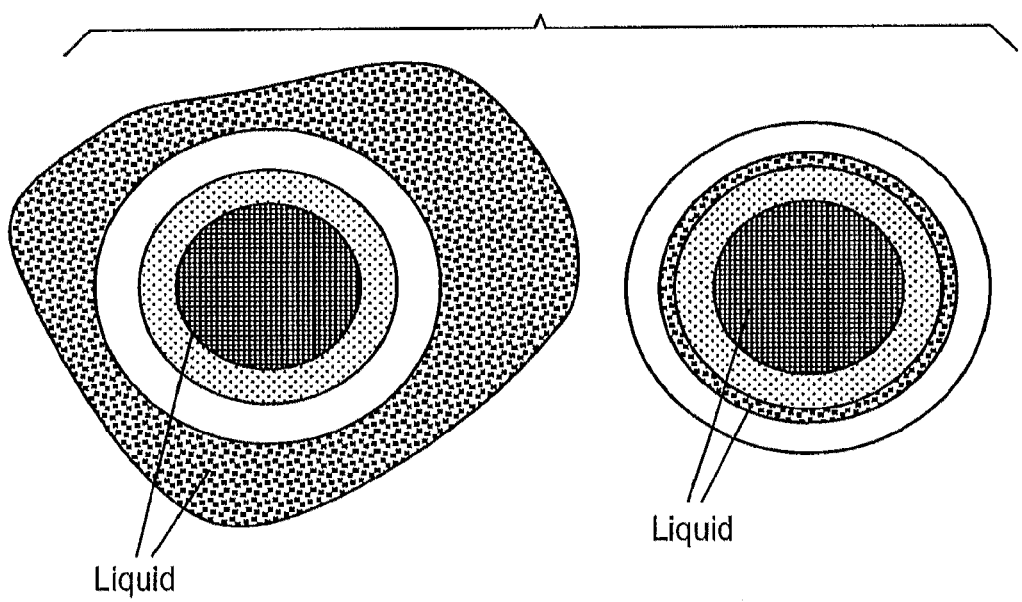

FIGS. 5(a) and 5(b) are schematic diagrams showing the formation of multi-shelled capsules with inner liquid cores and second liquid regions between the inner and outer shells according to embodiments disclosed herein.

Figure 6A:
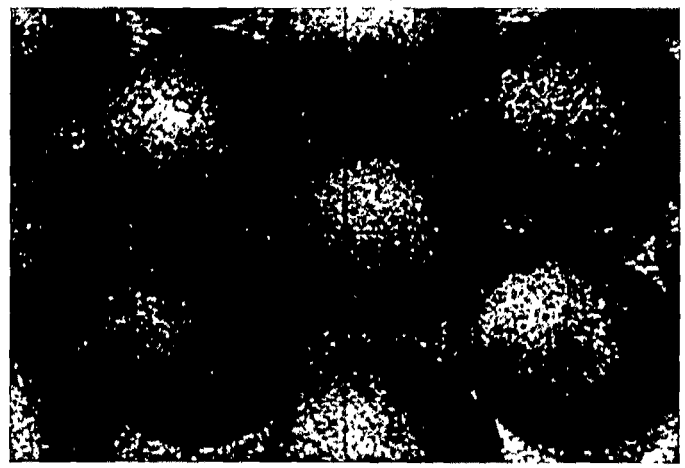
Figure 6B:

FIG. 6 shows that either spherical or ovoid capsules can be obtained according to embodiments disclosed herein.

DETAILED DESCRIPTION

As used herein, the term "smoking article" includes any material, article or device that is typically used to enjoy tobacco or tobacco substitutes by inhalation or smoking, including but not limited to cigars, cigarettes, pipe tobacco, loose or "roll-your-own" tobacco, electrically heated cigarettes, and the like.

As used herein, the term "smokeless tobacco" includes tobacco intended to be enjoyed in some manner other than inhalation or smoking, e.g., taken orally. Examples include snuff, pouched tobacco including snus, dip, plug tobacco, and the like.

As used herein, the term "tobacco product" includes both smoking articles and smokeless tobacco.

As used herein, the terms "flavorant" and "flavorant composition" denote organoleptic compounds and compositions that are applied to a substrate or article, at least in part in order to alter the taste or aroma characteristics of the substrate or article during consumption thereof.

A "liquid flavorant composition" as used herein denotes a flavorant composition that is in a liquid form, or can be rendered into liquid form by dissolution, suspension, or similar processes, under conditions typically encountered for the storage of the flavorant composition or of the article to which the flavorant composition is to be applied. A liquid flavorant composition may include high viscosity liquid compositions.

As used herein, the term "shell-forming polymeric material" denotes polymeric materials that can be cross-linked, dried, or otherwise hardened to form a shell, e.g., as part of a capsule. The term "first shell-forming polymeric material" denotes a shell-forming polymeric material that is substantially impermeable to one or more liquid flavorant compositions, at least in hardened form.

As used herein, the term "substantially impermeable" denotes a level of permeability sufficient that only a minor portion, if any, of the liquid being encapsulated within the substantially impermeable material can diffuse through the material over a period of time. This period of time is generally equivalent to a typical storage time for the consumable product, plus the typical storage time for the encapsulated flavorant composition.

As used herein, the term "hardening" denotes a curing, cross-linking, precipitation, drying, or other chemical or physical change to, or in, the polymeric material that renders the material into a shell that is less permeable to one or more components of the liquid flavorant composition and/or more structurally and/or dimensionally stable (i.e., able to withstand stress without rupture) and/or less permeable than the shell-forming polymeric material prior to hardening. The term "hardenable" denotes a material capable of undergoing hardening. A material that has undergone hardening may be resilient and/or flexible.

As used herein, the term "substantially insoluble" denotes a material that will not form a solid solution with the second polymeric material. Instead, most (if not all) of the material will undergo phase separation from the second polymeric material or from the second shell-forming polymeric material at least as early as the hardening of the second shell-forming polymeric material to form the outer shell.

As used herein, the terms "substantially spherical" and "substantially ovoid" denote generally spherical and ovoid shapes, respectively, and do not exclude slight departures or variations from the strict geometrical definitions of "spherical" and "ovoid."

As used herein, the term "about" when used in conjunction with a stated numerical value or range has the meaning reasonably ascribed to it by a person skilled in the art, i.e. denoting somewhat more or somewhat less than the stated value or range, to within a range of ±10% of the stated value.

Formation of core-shell capsules using a co-extrusion process depends on numerous parameters. These include the physical properties of the materials used (e.g., their viscosity, density, and interfacial tension), as well as processing conditions (flow rates, temperatures, amplitude and frequency of vibration of nozzle, the use of a submerged nozzle or non-submerged nozzle, and the geometry of nozzle such as the diameters of the inner and outer orifices). The influences of each of these factors is not isolated, but rather a complex interplay exists among them. Thus, using only an extrusion process to obtain core-shell capsules having desired properties, in particular having sufficient shell thickness, may be difficult or impossible. As disclosed herein, providing capsules with an inner and an outer shell of hardened second shell-forming polymeric material can overcome some of these difficulties.

In one embodiment, a method is provided for encapsulating a liquid flavorant composition, by co-extruding a first liquid flavorant composition and a first shell-forming polymeric material to form core-shell droplets containing an inner core that contains the first liquid flavorant composition, and an outer layer containing the first shell-forming polymeric material.

This droplet is preferably formed by a pair of concentric nozzles, with the liquid flavorant composition being passed through the inner nozzle, and the first shell-forming polymeric material passing through the outer nozzle. Droplet formation can include vibration or the passing of a gas or vapor stream near the nozzle in order to dislodge the droplet from the nozzle.

For example, droplet formation can take place in a Spherisator 2002 Mark II (Brace GmbH), desirably operating at a frequency ranging between about 20 Hz and about 200 Hz, more particularly between about 60 Hz and about 100 Hz, even more particularly between about 70 Hz and about 85 Hz, still more particularly between about 70 Hz and about 80 Hz. The amplitude applied to the electromagnetic shaker of the device is desirably between about 100 mV and about 2000 mV, more particularly between about 330 mV and about 1000 mV, even more particularly between about 350 mV and about 450 mV. Nozzle diameters generally range between about 0.5 mm and about 2 mm, more particularly between about 0.9 mm and about 1.5 mm, for the inner, core-forming nozzle, and between about 1.5 mm and about 3 mm, more particularly between about 2 mm and about 2.5 mm, for the outer, shell-forming nozzle. Pressure in the core-forming stream of the co-extruder is generally between about 40 mbar and about 80 mbar, more particularly between about 50 mbar and about 65 mbar, while pressure in the shell-forming stream of the co-extruder is generally between about 90 mbar and about 150 mbar, more particularly between about 100 mbar and about 130 mbar. The diameter of the co-extruded capsules typically ranges from about 1 to about 7 mm.

FIGS. 1(a), 1(b), 1(c), and 1(d) are schematic illustrations of alternate forms which can be taken by a co-extruded core-shell droplet at a nozzle. In FIG. 1(a) the shell-forming polymeric material tends to release relatively easily from the surface of the nozzle, whereas in FIG. 1(b) the shell-forming polymeric material tends to cling to the surface of the nozzle In FIG. 1(c) the co-extruded droplet tends to extend relatively far before assuming a rounded or globular shape, whereas in FIG. 1(d) the co-extruded droplet tends to form a substantially rounded or globular shape before releasing from the nozzle. The co-extruded core-shell droplet could take other forms, including mixed or intermediate forms, apart from those illustrated. Droplet shape may be indicative of process parameters so that observation thereof may guide formation of desirable capsules.

Once free of the nozzle, the first shell-forming polymeric material can flow around the core-shell droplet to completely, or substantially completely, surround the liquid flavorant composition.

Liquid flavorant compositions suitable for use herein include both hydrophilic, generally aqueous, compositions, and hydrophobic, generally oil-based, compositions. In general, these compositions contain one or more flavorant molecules, which can be dissolved or suspended in a liquid vehicle or solvent, particularly if they are not naturally obtained in liquid form. Examples of suitable flavorants include, but are not limited to, menthol, mint, such as peppermint or spearmint, chocolate, licorice, citrus and other fruit flavors, gamma octalactone, vanillin, ethyl vanillin, cinnamon, methyl salicylate, linalool, bergamot oil, geranium oil, lemon oil, ginger oil, tobacco extract, phenylacetic acid, solanone, megastigmatrienone, 2-heptanone, benzylalcohol, cis-3-hexenyl acetate, valeric acid, valeric aldehyde, etc. Flavorants in a solution or suspension of vegetable oil have been found to be particularly useful.

The first shell-forming polymeric material preferably contains a cross-linkable polysaccharide, a protein, or a wax. When hardened to form a shell, the first shell-forming polymeric material forms a substantially impermeable barrier to the first liquid flavorant composition. Preferred cross-linkable polysaccharides include alginates, pectins, carrageenans, chitosans, dextrans, and combinations and mixtures of these. Preferred proteins include gelatins. Particularly preferred as the first shell-forming polymeric material are alginate salts with monovalent cations, such as sodium alginate. Preferably, the alginate is coextruded as an aqueous solution having an alginate concentration ranging between about 1 and about 5 wt %, preferably between about 2 and about 2.5 wt %.

The formed droplet is then treated to harden the first shell-forming polymeric material to form an inner shell around an inner core comprising the first liquid flavorant composition. The hardening process may simply involve cooling, e.g., if the first shell-forming polymeric material is a wax or a gelatin.

Hardening may, however, involve more complex processes, particularly when the first shell-forming polymeric material contains a polysaccharide. For example, if the first shell-forming polymeric material comprises sodium alginate, the hardening process will preferably involve an ionic substitution reaction, with a divalent metal ion displacing sodium, and effectively cross-linking the alginate polymer. Other polysaccharides undergo similar ionic cross-linking reactions during hardening. In addition, hardening may involve drying in order to remove excess moisture from the shell, and to render the shell less tacky. This type of hardening process may be carried out by dropping the droplets into a bath of aqueous divalent metal ion, preferably calcium ion. As an example, a bath of aqueous $CaCl_2$ can be used. Alternatively, droplets can be sprayed with a mist of aqueous $CaCl_2$ or other divalent metal ion after they have left the concentric nozzles. Either way, calcium ions on the surface of the droplet displace sodium ions and cross-link the alginate polymer. As the length of time the droplets spend in contact with the calcium ion solution increases, the depth of penetration of calcium ions into the outer layer increases, and so does the depth of hardened polymer. Desirably, the $CaCl_2$ solution is applied as an aqueous solution having a concentration between about 3 wt % and about 10 wt %, more particularly, having a concentration of about 5 wt %. The $CaCl_2$ contact time and solution concentration, along with subsequent washing to remove calcium ions (described more fully herein), can also affect the formation of a coating later and/or the hardening of the coating layers.

FIG. 2 shows an illustrative example of how the capsule, containing the encapsulated first liquid flavorant composition and the inner shell of the hardened first polymeric material, is then coated with one or more coating layers containing a second shell-forming polymeric material to form a multi-shelled capsule. This multi-shelled capsule has shells of hardened shell-forming polymeric material surrounding a core. A variety of processes for coating capsules, such as curtain coating, coacervation, etc., will provide acceptable results; however, an exemplary coating process is described herein and illustrated in FIG. 2. The capsules described above, having the inner shell but not yet an outer shell, can be harvested by filtration from their aqueous bath (in FIG. 2, a $CaCl_2$ solution), and after washing to remove excess divalent metal ions, and draining to remove excess surface water, are deposited into a solution of second shell-forming polymeric material, typically while stirring (in FIG. 2, the solution of second shell-forming polymeric material is an alginate solution). The capsules are maintained in this solution for a period of time sufficient to allow the coating layer to grow to its desired thickness, the time typically ranging from about 30 seconds to several hours, depending on the desired thickness. At the conclusion of this time, water is added to dilute the solution of second shell-forming polymeric material, and slow or stop the growth of the coating layer. The coated capsules are separated from the coating solution by filtration or decanting, and additional water is added to remove excess shell-forming polymeric material. This separation and diluting process may be repeated several times, and the resulting coated capsules may then be optionally dried, e.g., by exposure to a stream of hot gas, such as in a tumble dryer.

Examples of suitable second shell-forming polymeric materials include cross-linkable polysaccharides, such as alginate, pectin, carrageenan, chitosan, and mixtures thereof.

Once the coated capsules have been formed, the second shell-forming polymeric material in the coating layer is hardened to form a multi-shelled capsule containing the capsule with the inner shell surrounded by an outer shell of hardened second shell-forming polymeric material. Hardening may be accomplished by contacting the second shell-forming polymeric material with the appropriate cross-linking agent. For example, if the second shell-forming polymeric material includes sodium alginate, a solution of calcium ions can be added to harden the coating layer. If the inner shell contains cross-linked alginate, there may be sufficient residual free calcium ion in the inner shell to migrate into the coating and cause cross-linking to occur, without need for additional calcium ions. The hardening may preferably begin during the coating step, for example by cross-linking during coating with residual calcium in the inner shell.

In some cases, the outer surface of the multi-shelled capsule will be somewhat adherent or tacky, in part due to the high moisture content therein. In one embodiment, the method of producing the multi-shelled capsules includes drying the capsules to reduce this tackiness. Drying in this way may also be regarded as a hardening step. It is desirable to dry the multi-shelled capsules while minimizing any disruption of their shells. A tumbling dryer will be suitable for this purpose. In order to limit the adherence of the multi-shelled capsules to the interior surfaces of the dryer, it is preferred to conduct the drying while introducing an inert gas, such as nitrogen, into the dryer.

The capsules produced by this process will be highly storage stable, and can effectively reduce or prevent migration and/or loss of the flavorant in the liquid flavorant composition during storage of articles and products incorporating the capsules.

FIG. 3 shows data obtained on the burst strength of 4.0 mm diameter multi-shelled capsules. In FIG. 3(a), the solution of second shell-forming polymeric material was 0.25% by weight of alginate, and it can be seen that the burst strength increased with increasing coating time. In FIG. 3(b), burst strength of capsules having various shell thicknesses from about 12 to 43 µm (in this figure, meaning a combined thickness of the inner and outer shells including any space between the shells) was measured using a Shimadzu EZ-Graph with a compression speed of 100 mm/min. The burst strength increased with increasing shell thickness. These graphs shows that the methods described herein are able to produce a capsule having a burst strength of about 6 to 11 N, preferably about 8 to 10 N.

The first and second shells are distinct from one another, and each which can have different thicknesses, mechanical strengths, thermal and/or moisture stability, degradation rates, and the like. As a result, the selection of the first and second polymeric materials can vary the physical and chemical properties of the resulting multi-shelled capsule.

Irrespective of the particular first and second shell-forming polymeric materials used to form the inner and outer shells, the outer shell, after hardening, contains an inner surface and an outer surface, such that the inner surface of the outer shell is separate and/or separable from the outer surface of the inner shell. The two shells can define a space between them when they are separated. Thus the two shells may be forced apart by osmotic pressure imposed by phase separation or by diffusion into the capsule, as explained more fully herein. The ability to provide different liquid flavorant compositions in the core and in a space between shells in the same capsule allows for the controlled release of different flavorant compositions as the article containing the capsule is consumed, providing a different and pleasing aesthetic effect to the consumer.

FIGS. 4(a)-(e) shows photomicrographs of cross sections of a multi-shelled capsule. In these figures, "i" represents the inside of the capsule and "o" represents the outside. FIG. 4(a) shows an image of a cross-section of a multi-shelled capsule according to embodiments described herein, with FIGS. 4(b)-(e) showing more details images at various points along the cross-section. A space between the first and second shells can be seen.

As seen in FIGS. 5(a) and 5(b), the encapsulated composition can comprise, in addition to the inner core with its first liquid flavorant composition, a second liquid composition (for example, a flavorant, the same or different from the flavorant or the first liquid flavorant composition) that contains one or more components that are substantially insoluble in the outer shell of the multi-shelled capsule.

In one such embodiment, illustrated schematically in FIG. 5(a), the initial capsule (having an inner shell around an inner core) is coated with a gel comprising a liquid that is substantially insoluble in the hardened second shell-forming polymeric material. Upon phase separation, this substantially insoluble component or components separates and migrates to a space between the two shells. Because the outer surface of the inner shell and the inner surface of the outer shell are separate and/or separable, osmotic pressure allows the migrating component of the second liquid flavorant composition to occupy and/or force its way between the shell surfaces. Upon hardening of the outer shell, this migrating component can form a liquid region that is at least partially in a space between the outer surface of the inner shell and the inner surface of the outer shell.

In another embodiment, illustrated schematically in FIG. 5(b), a second flavorant liquid composition is introduced between the inner and outer shells by placing the multi-shelled capsule or the coated first capsule (the capsule having an inner shell and a coating layer) in a solution or suspension of the second liquid flavorant composition, before the second shell-forming polymeric material is completely hardened. Because the inner surface of the outer shell is separate and/or separable from the outer surface of the inner shell, the second liquid flavorant composition can penetrate the outer shell or coating layer by diffusion, and create and/or occupy a space between the inner and outer shells, or between the inner shell and the coating layer, thereby forming a liquid region at least partially between the outer surface of the inner shell and the inner surface of the outer shell. The second shell-forming polymeric material is then subjected to hardening, or additional hardening as the case may be.

The result of either of these embodiments is a capsule having a first liquid flavorant composition in the core and a second, optionally different, liquid flavorant composition at least partially in a region between the inner and outer shells. This allows for release of flavorants at different times during the consumption of an article incorporating such capsules.

Smoking Articles and Smokeless Tobacco

Flavorants used with tobacco smoking articles, e.g., menthol, can migrate from the tobacco to which the menthol was applied to other parts of the smoking article, or can migrate out of the smoking article entirely. This decreases the level of flavorant available when the article is consumed, often requiring that increased levels of flavorants be applied to the article. Applying increased amounts of flavorant means undesired added costs in production. The use of encapsulated flavorants as described herein can overcome these problems.

For example, one or more capsules containing one flavorant, e.g. menthol, as the flavorant in the first and second liquid flavorant compositions can be incorporated into the tobacco rod or filter of a smoking article, such as a cigarette. As the cigarette is smoked, the second polymeric coating can become degraded by the mainstream smoke flowing past the capsule, thereby releasing the menthol from the second liquid flavorant composition to the consumer. Later, as the cigarette continues to be smoked, the menthol in the first liquid flavorant composition in the core is released to the mainstream smoke as the inner shell degrades. The result is that the consumer enjoys increased menthol flavor at different points in the smoking experience.

In another example, one or more capsules containing one flavorant, e.g., menthol as a flavorant in the first liquid flavorant composition, and a different flavorant, e.g. tobacco extract, as a flavorant in the second liquid flavorant composition, can be incorporated into the tobacco rod and/or filter of a cigarette. As the cigarette is smoked, the outer shell degrades in the moist, hot mainstream smoke, releasing tobacco flavor, thereby enhancing the tobacco flavor provided by tobacco in the cigarette. As smoking continues, the inner shell can become degraded, releasing menthol flavor into the mainstream smoke.

In either of these examples, multiple capsules can be disposed in the cigarette, and their disposition can have an effect on the delivery of flavorant to the consumer. For instance, disposing multiple capsules having the same or similar thicknesses of shells at the same or similar location in the cigarette can result in an increase of a particular flavor over a relatively short time. Because each of the capsules is subjected to similar degradation conditions, the shells will degrade at similar rates, releasing their flavorants at similar times.

In another embodiment, it is possible to vary the release rates of flavorant from different capsules by varying the thickness and other mechanical properties of the inner and outer shells. This allows for the capsules to be engineered for different locations in the article, thereby controlling flavorant release with time. For example, capsules having relatively thick shells can be disposed in or near the filter, while capsules having relatively thin shells can be disposed in the tobacco rod near the lit end of a cigarette. The thick shelled capsules will retain their flavorant for a longer time when subjected to mainstream smoke, so that the consumer continues to experience flavorant release later in the smoking experience. Cigarettes including encapsulated flavoring are described in U.S. Patent Application Publication Nos. 2005/0172976 and 2008/0017206 each of which is herein incorporated by reference in its entirety.

Similarly, capsules can be added to smokeless tobacco products, wherein flavorant release results from mechanical rupture of the capsules during mastication or from dissolution of the capsules in saliva. By including capsules having varying shell thicknesses, the release profile for delivery of the flavorant or flavorants over time can be controlled, so that the consumer experiences certain flavors early in the experience and other flavors later on, or so that the consumer experiences a more continuous, consistent level of a particular flavorant.

As shown by FIG. 6, in addition to providing control over the structure of the capsules, their mechanical properties, and their delivery characteristics, the method disclosed herein can provide control over the overall capsule morphology. By varying the parameters of the co-extrusion process, capsule shape can be varied between substantially spherical to substantially ovoid. Among the advantages of various morphologies, an ovoid type of capsule may require reduced force required for bursting (because forced is concentrated at a tip of the capsule), which may be desirable in certain applications.

In yet another embodiment, one or more multi-shelled capsules as described herein are incorporated in filter of a cigarette so that, at a time chosen by the smoker, they may be crushed to release liquid flavorant into the filter. Preferably, such capsules are ovoid-shaped to facilitate mechanical rupture. Cigarettes and filter subassemblies with squeezable flavor capsules are described in U.S. Patent Application Publications 2007/0012327 and 2006/0174901, each of which is herein incorporated by reference in its entirety.

EXAMPLES

Examples 1

A mixture of flavorant (9670-102A) in vegetable oil was fed through the inner, or core, nozzle (1.0 mm diameter) of a Brace GmbH Spherisator 2002 Mark II 1410-087 co-extruder under a pressure of 55 mbar. A aqueous solution of 2 wt % sodium alginate (a first shell-forming polymeric material) was fed through the outer, or shell-forming, nozzle of the co-extruder (2.5 mm diameter) under a pressure of 100 mbar. The frequency of vibration was 80 Hz, and the amplitude of vibration was 350 mV. The coated cores produced by the co-extrusion were contacted with an aqueous hardening solution containing 5 wt % calcium chloride and filtered and washed with additional aqueous hardening solution containing 5 wt % calcium chloride. Some of the coated cores that were produced were undesirably small "satellite" capsules (which can be screened or separated from desirable capsules) or had cores that were not perfectly centered. A small amount of oil was observed on the surface of the suspension of coated cores, believed to originate from broken capsules and/or unincorporated core material.

The capsules were washed and screened and were then grown by the following process to produce multi-shelled capsules. The capsules were added to an aqueous solution of 0.25 wt % sodium alginate (the second shell-forming polymeric material), stirred for 20 minutes, and deionized water was then added to dilute the alginate solution. (It was found that using alginate concentrations substantially greater than 0.25 wt % resulted in undesired aggregation of capsules.) The capsules were removed from the solution, and contacted with 5 wt % calcium chloride, filtered, washed with deionized water, and contacted with room temperature nitrogen in a tumbling dryer to dry the capsules. Relatively uniform capsules with no observed aggregation were obtained. The resulting multi-shelled capsules weighed between about 35 mg and about 39 mg per capsule, with an average weight of about 36 mg/capsule.

Example 2

The procedure described above in Example 1 was generally followed, except that the flavorant was fed through the inner nozzle under a pressure of 60 mbar, and the alginate solution was fed through the outer nozzle under a pressure of 125 mbar. Some of the coated cores produced were satellites or had cores that were not perfectly centered. After drying, several of the capsules were broken. The weight of the capsules ranged between about 30 mg and about 35 mg per capsule, with an average weight of about 32 mg/capsule. The burst strength of the capsules was measured and found to range between about 3.5 N and about 16.7 N.

Example 3

The procedure described in Example 1 was generally followed, except that the vibration frequency was 100 Hz, the outer nozzle pressure was 105 mbar. Almost no small capsules were observed, although several non-encapsulated beads were observed. The filtered coated cores were added to an aqueous solution containing 0.25 wt % sodium alginate and 1.0 wt % polyvinylpyrrolidone ("PVP"), stirred for 20 minutes, diluted with water, removed from solution, and filtered directly without addition of more calcium chloride. The filtered capsules were dried in a tumbling dryer, as in Example 1. Average capsule weight was found to be 33.8 mg/capsule, but the PVP did not prevent the formation of aggregates.

Example 4

The procedure described above for Example 1 was generally followed, except that a different flavorant (9814-57) in vegetable oil was used, along with the following additional changes.

As a first sub-example, the feed through the inner nozzle was at a pressure of 60 mbar, the feed through the outer nozzle was at a pressure of 130 mbar, using a frequency of 50 Hz and an amplitude of 300 mV. The output from the nozzle appeared as FIG. 1(a). The result was many non-core/shell spheres (that is, spheres without a core) and an unstable process, along with non-centered cores and an oil layer.

As a second sub-example, the feed through the inner nozzle was at a pressure of 58 mbar, the feed through the outer nozzle was at a pressure of 125 mbar, using a frequency of 50 Hz and an amplitude of 300 mV. The output from the nozzle appeared as FIG. 1(a). The result was many non-core/shell spheres and an oil layer. The resulting capsules were sticky, easy to break, and of non-uniform size.

As a third sub-example, the feed through the inner nozzle was at a pressure of 57 mbar, the feed through the outer nozzle was at a pressure of 130 mbar, using a frequency of 80 Hz and an amplitude of 350 mV. The output from the nozzle appeared as FIG. 1(b). The result was no observed non-core/shell spheres and several satellite capsules, which were spherical.

As a fourth sub-example, the feed through the inner nozzle was at a pressure of 60 mbar, the feed through the outer nozzle was at a pressure of 115 mbar, using a frequency of 80 Hz and an amplitude of 350 mV. The output from the nozzle appeared as FIG. 1(a). The result was many non-core/shell spheres and an oil layer. The resulting capsules were easy to break, and of non-uniform size.

Example 5

The procedure described above for Example 1 was generally followed, except flavorant 9814-57 in vegetable oil was fed through the inner nozzle at a pressure of 60 mbar, and the sodium alginate solution was fed through the outer nozzle at a pressure of 130 mbar. The output from the nozzle appeared as FIG. 1(a). Capsules and several spheres that were non-core/shellspheres were produced. At least some of the cores appeared highly off-center, and small. To the 0.25 wt % alginate solution was added 0.1 wt % green food coloring, to enhance visualization of the second alginate layer (the outer shell). The dried capsules were desirably small (not satellites), hard, and ovoid or egg shaped.

Example 6

Figure 1B:
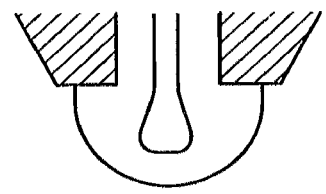
Figure 1C:
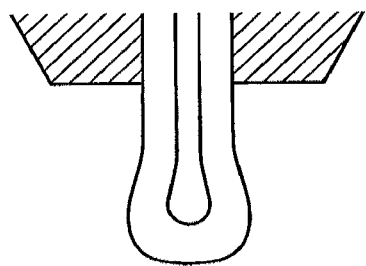
Figure 1D:
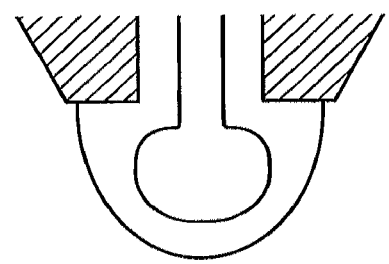

The procedure described above for Example 5 was followed, except that the nozzle output was made to appear as in FIG. 1(b). This resulted in desirably small capsules that were ovoid or egg shaped.

Example 7

The procedure described above for Example 1 was generally followed, except that the core material was vegetable oil with blue dye fed at 60-100 mbar and the shell was fed at 90-140 mbar. The frequency was 90 Hz and the amplitude was 400 mV. This resulted in small capsules with off-centered cores.

Example 8

The procedure described above for Example 1 was generally followed, except that the core material was vegetable oil with blue dye, along with the following additional changes.

As a first sub-example, the core material was fed at 65 mbar through a 0.9 mm nozzle and the shell was fed at 90-140 mbar. The frequency was 90 Hz and the amplitude was 400 mV. The output from the nozzle appeared as FIG. 1(c). The process was unstable. Small capsules with off-centered cores were produced.

As a second sub-example, the procedure for the first sub-example was used, with the following changes. The shell material was fed through a 2.2 mm nozzle at 115 mbar and the core material was fed at 70 mbar. The frequency was 80 Hz and the amplitude was 350 mV. The output from the nozzle appeared as FIG. 1(d). The process was stable with desirably small capsules produced. Cores were not centered.

As a third sub-example, the procedure for the first sub-example was used, with the following changes. The core was fed through a 1.0 mm nozzle at 65 mbar and the shell was fed through a 2.5 mm nozzle at 120 mbar. The frequency was 80 Hz and the amplitude was 350 mV. The output from the nozzle appeared as FIG. 1(a). The process was stable with no satellite capsules produced. There were non-core/shell spheres. Cores were not centered.

As a fourth sub-example, the procedure for the third sub-example was used, with the following changes. The shell material was fed at 125 mbar and the core material was fed at 80 mbar. The frequency was 100 Hz. The output from the nozzle appeared as FIG. 1(a). The process was stable with no small capsules produced. There were non-core/shell spheres. The centering of the core was better than in the third sub-example.

As a fifth sub-example, the procedure for the fourth sub-example was used, with the following changes. The shell material was fed at 115 mbar and the core material was fed at 75 mbar. The output from the nozzle appeared as FIG. 1(d). Small capsules appeared as a by-product, and cores were not centered.

Example 9

The procedure described above for Example 1 was generally followed, except that the inner nozzle diameter was 0.9 mm and the outer nozzle diameter was 2.2 mm; the pressure of material fed to the inner nozzle was varied, so that 64 mbar, 70 mbar, 75 mbar, 80 mbar, 85 mbar, and 87 mbar pressures were used. The pressure of material fed to the outer nozzle was kept at 115 mbar. The frequency of vibration was 90 Hz. The process did not produce satellite capsules. As the inner nozzle pressure increased, the centering of the core in the capsules was improved. At an inner nozzle pressure of 87 mbar, some of the capsules produced were easily broken. Capsules produced at an inner nozzle pressure of 85 mbar were dried for 2 hours, and contacted with 0.25 wt % sodium alginate solution for 20 minutes while stirring at 250 rpm. The particles were washed several times with 1000 ml aliquots of water, which was then removed. The washed capsules were then placed into 100 ml of 5 wt % $CaCl_2$, filtered, and washed with several 500 ml aliquots of water. Egg-shaped or ovoid capsules were produced.

While the invention has been described in detail with reference to preferred embodiments thereof, it will be apparent to one skilled in the art that various changes can be made, and equivalents employed, without departing from the scope of the invention.

All of the above-mentioned references are herein incorporated by reference in their entirety to the same extent as if each individual reference was specifically and individually indicated to be incorporated herein by reference in its entirety.

What is claimed is:

1. A method for encapsulating a liquid flavorant composition in a multi-shelled capsule, comprising:
    (a) co-extruding a first liquid flavorant composition and a first shell-forming polymeric material to form a core-shell droplet;
    (b) hardening the first shell-forming polymeric material of the droplet to form an inner shell around an inner core, the inner core comprising the first liquid flavorant composition;
    (c) coating the inner shell with a coating layer comprising a second shell-forming polymeric material; and
    (d) hardening the second shell-forming polymeric material by contacting the second shell-forming polymer with polyvalent metal ions present in or on the inner shell, to form an outer shell of the multi-shelled capsule,
    wherein the co-extruding step comprises using a co-extruder comprising an inner nozzle having a diameter of between about 0.5 mm and 2 mm, and an outer nozzle having a diameter of between about 1.5 mm and 3 mm, and
    wherein the first liquid flavorant composition is fed to the inner nozzle at between about 40 mbar and 80 mbar, and the first shell-forming polymeric material is fed to the outer nozzle at between about 100 mbar and 130 mbar.

2. The method of claim 1, wherein an inner surface of the outer shell is separated from an outer surface of the inner shell.

3. The method of claim 2,
    further comprising forming a second liquid region at least partially between the outer surface of the inner shell and the inner surface of the outer shell.

4. The method of claim 1, wherein the multi-shelled capsule has a burst strength measured using a Shimadzu EZ-Graph with a compression speed of 100 mm/min of between about 6 and 11 N.

5. The method of claim 1, wherein said first liquid flavorant composition comprises a first flavorant selected from the group consisting of menthol, mint, chocolate, licorice, citrus and other fruit flavors, gamma octalactone, vanillin, ethyl vanillin, cinnamon, methyl salicylate, linalool, bergamot oil, geranium oil, lemon oil, ginger oil, tobacco extract, phenylacetic acid, solanone, megastigmatrienone, 2-heptanone, benzylalcohol, cis-3-hexenyl acetate, valeric acid, valeric aldehyde, and mixtures thereof.

6. The method of claim 1, wherein the multi-shelled capsule is substantially spherical or ovoid.

7. The method of claim 1, wherein said hardening the second shell-forming polymeric material comprises drying in a tumbling dryer.

8. A method for encapsulating a liquid flavorant composition in a multi-shelled capsule, comprising:
    (a) co-extruding a first liquid flavorant composition and a first shell-forming polymeric material to form a core-shell droplet;

(b) hardening the first shell-forming polymeric material of the droplet to form an inner shell around an inner core, the inner core comprising the first liquid flavorant composition;

(c) coating the inner shell with a coating layer comprising a second shell-forming polymeric material; and (d) hardening the second shell-forming polymeric material by contacting the second shell-forming polymer with polyvalent metal ions present in or on the inner shell, to form an outer shell of the multi-shelled capsule, wherein an inner surface of the outer shell is separated from an outer surface of the inner shell, the method further comprising forming a second liquid region at least partially between the outer surface of the inner shell and the inner surface of the outer shell by one of the following:

(a') coating the inner shell with a gel comprising one or more components that are substantially insoluble in the second shell-forming polymeric material, whereby before or upon hardening of the second shell-forming polymeric material the second liquid region is formed and comprises the one or more components that are substantially insoluble; or (b') before the second shell-forming polymeric material is completely hardened, contacting either the coated inner shell or the multi-shelled capsule with a second liquid flavorant composition for a time and under conditions sufficient for at least a portion of said second liquid flavorant composition to move through said outer shell or said coating layer to form said liquid region, followed by hardening of the second shell-forming polymeric material.

9. The method of claim 8, wherein said first shell-forming polymeric material comprises a cross-linkable polysaccharide, a hardenable protein, or a hardenable wax.

10. The method of claim 9, wherein said cross-linkable polysaccharide is selected from the group consisting of alginates, pectins, carrageenans, chitosans, dextrans, and combinations or mixtures thereof.

11. The method of claim 10, wherein the first and second shell-forming polymeric materials each comprise a cross-linkable alginate.

12. The method of claim 8, wherein the multi-shelled capsule has a burst strength measured using a Shimadzu EZ-Graph with a compression speed of 100 mm/min of between about 6 and 11 N.

13. The method of claim 8, wherein said first liquid flavorant composition comprises a first flavorant selected from the group consisting of menthol, mint, chocolate, licorice, citrus and other fruit flavors, gamma octalactone, vanillin, ethyl vanillin, cinnamon, methyl salicylate, linalool, bergamot oil, geranium oil, lemon oil, ginger oil, tobacco extract, phenylacetic acid, solanone, megastigmatrienone, 2-heptanone, benzylalcohol, cis-3-hexenyl acetate, valeric acid, valeric aldehyde, and mixtures thereof.

14. The method of claim 8, wherein the multi-shelled capsule is substantially spherical or ovoid.

15. The method of claim 8, wherein said hardening the second shell-forming polymeric material comprises drying in a tumbling dryer.

16. A method for encapsulating a liquid flavorant composition in a multi-shelled capsule, comprising:

(a) co-extruding a first liquid flavorant composition and a first shell-forming polymeric material to form a core-shell droplet;

(b) hardening the first shell-forming polymeric material of the droplet to form an inner shell around an inner core, the inner core comprising the first liquid flavorant composition;

(c) coating the inner shell with a coating layer comprising a second shell-forming polymeric material; and (d) hardening the second shell-forming polymeric material by contacting the second shell-forming polymer with polyvalent metal ions present in or on the inner shell, to form an outer shell of the multi-shelled capsule, wherein said co-extruding step comprises using a co-extruder having an electromagnetic shaker operating at a frequency of between about 20 and 200 Hz and an amplitude of between about 100 and 2000 mV.

17. The method of claim 16, wherein the multi-shelled capsule has a burst strength measured using a Shimadzu EZ-Graph with a compression speed of 100 mm/min of between about 6 and 11 N.

18. The method of claim 16, wherein said first liquid flavorant composition comprises a first flavorant selected from the group consisting of menthol, mint, chocolate, licorice, citrus and other fruit flavors, gamma octalactone, vanillin, ethyl vanillin, cinnamon, methyl salicylate, linalool, bergamot oil, geranium oil, lemon oil, ginger oil, tobacco extract, phenylacetic acid, solanone, megastigmatrienone, 2-heptanone, benzylalcohol, cis-3-hexenyl acetate, valeric acid, valeric aldehyde, and mixtures thereof.

19. The method of claim 16, wherein the multi-shelled capsule is substantially spherical or ovoid.

20. The method of claim 16, wherein said first shell-forming polymeric material comprises a cross-linkable polysaccharide, a hardenable protein, or a hardenable wax.

21. The method of claim 20, wherein said cross-linkable polysaccharide is selected from the group consisting of alginates, pectins, carrageenans, chitosans, dextrans, and combinations or mixtures thereof.

22. The method of claim 21, wherein the first and second shell-forming polymeric materials each comprise a cross-linkable alginate.

23. The method of claim 16, wherein said hardening the second shell-forming polymeric material comprises drying in a tumbling dryer.

\* \* \* \* \*